United States Patent [19]

Young

[11] 4,255,600
[45] Mar. 10, 1981

[54] ZSM-12 CYCLOOLEFIN DIMERIZATION

[75] Inventor: L. Brewster Young, Skillman, N.J.

[73] Assignee: Mobil Oil Corporation, Fairfax, Va.

[21] Appl. No.: 100,592

[22] Filed: Dec. 5, 1979

[51] Int. Cl.$^3$ ...................... C07C 175/10; C07C 2/76
[52] U.S. Cl. ................................ 585/362; 252/455 Z
[58] Field of Search ........................................ 585/362

[56] References Cited

U.S. PATENT DOCUMENTS

| | | |
|---|---|---|
| 3,832,449 | 8/1974 | Rosinski . |
| 3,970,544 | 7/1976 | Rosinski . |

*Primary Examiner*—Veronica O'Keefe
*Attorney, Agent, or Firm*—C. A. Huggett

[57] ABSTRACT

A process for the selective dimerization of cycloolefins having from 5 to about 12 carbon atoms is provided. The process comprises contacting of the olefin in the liquid phase with ZSM-12 at temperatures of 75° to 400° C.

11 Claims, No Drawings

ZSM-12 CYCLOOLEFIN DIMERIZATION

BACKGROUND OF THE INVENTION

1. Field of the Invention

The invention relates to a method for dimerizing cyclo-olefins having from 5 to about 12 carbon atoms by passing such olefins over a ZSM-12 zeolite.

2. Description of the Prior Art

It has long been known to contact various hydrocarbon fractions with acidic catalysts generally and, in particular, with solid siliceous acidic catalysts--including those referred to as crystalline aluminosilicate zeolites. Contact of hydrocarbon feeds with such acid catalysts is carried out for a wide variety of reactions, including cracking, isomerization, hydrocracking, etc. Representative U.S. patents disclosing and claiming contacting various hydrocarbon fractions with crystalline aluminosilicates are U.S. Pat Nos. 3,140,249; 3,140,251; 3,140,253; and 3,140,322.

Oligomerization and polymerization of olefins in the gas phase over various zeolites such as Linde A, X and Y is also known to the art. A major problem associated with such reactions is the formation of very high boiling hydrocarbons which remain on the catalyst and block the active sites. This causes rapid aging of the catalysts.

Conversion of $C_2$ to $C_5$ olefins over ZSM-5 catalysts is also known to the art. In U.S. Pat. No. 3,960,978, a process for producing a gasoline fraction containing predominately olefinic compounds which comprises contacting $C_2$ to $C_5$ olefins with a ZSM-5 type crystalline aluminosilicate zeolite at a temperature of from about 500° F. to about 900° F. is disclosed. In U.S. Pat. No. 3,827,968, a two step process comprising oligomerization of a gaseous $C_2$ to $C_5$ olefin containing stream by contacting with a ZSM-5 type of zeolite at a temperature of from about 550° F. to 850° F. followed by aromatization of the product of the oligomerization reaction is disclosed. The processes disclosed in these patents differ from that of the present invention in that they employ a different catalyst and are not directed to conversion of cyclo-olefins.

Zeolite ZSM-12 and hydrocarbon conversion over ZSM-12 are disclosed in U.S. Pat. No. 3,832,449 and U.S. Pat. No. 3,970,544 respectively. In U.S. Pat. No. 3,775,501, a process for the production of aromatics which comprises passing a mixture of air or oxygen and a hydrocarbon having from 2 to 16 carbon atoms over a ZSM-12 zeolite at a temperature between about 500° F. and 1300° F. is disclosed. These patents do not disclose the dimerization process of the present invention.

In U.S. Pat. No. 4,021,502, a process is disclosed in which gaseous $C_2$ to $C_5$ olefins are converted into gasoline blending stock by passage over ZSM-12 at temperatures of from about 450° F. to about 1200° F. The process disclosed in this patent differs from that of the present invention in that the process of the present invention is directed to dimerization of cyclo-olefins.

SUMMARY OF THE INVENTION

In accordance with the present invention, there has been discovered a process for the selective dimerization of cyclo-olefins having from 5 to about 12 carbon atoms which process comprises contacting such olefins, in the liquid phase, with a ZSM-12 zeolite at temperatures from about 75° to about 400° C.

It has been found that the present process provides selective conversion of the cyclo-olefin feed to dimer products. The product of the present reaction thus contains primarily cyclo-olefin dimer and little or no polymer, light cracked products, paraffins, etc. While not wishing to be bound by any theory, it is believed that this desirable result is brought about by contacting the cyclo-olefin feed with the ZSM-12 zeolite at low temperatures of from about 100° to about 300° C. The low temperature operation allows the dimerization reaction to proceed but does not favor undesirable side reactions such as cracking.

A significant feature of the present process is the liquid phase contacting of the olefin feed and the ZSM-12 zeolite. Again, while not wishing to be bound by any theory, it is believed that contacting the olefin feed and ZSM-12 zeolite in the liquid phase results in substantially increased catalyst life. This is because operation in the liquid phase tends to "wash" higher boiling products from the surface of the ZSM-12, thus preventing the build-up of such products and the concomitant blocking of active sites. By way of comparison, if the reaction were run in the gas phase, the higher boiling products would tend to deposit on the surfaces of the ZSM-12 catalyst and cause severe aging by blocking the active sites.

In accordance with the present invention, cyclo-olefins having from 5 to 12 carbon atoms, preferably from 5 to about 10 carbon atoms, are contacted with a catalyst comprising a ZSM-12 zeolite, in the liquid phase, at temperatures of from about 75° to about 400° C. and a WHSV, based on zeolite, of from about 1 to about 100. Preferred are temperatures of from 100° to about 300° C. It will be appreciated that the pressure employed must be sufficient to maintain to system in the liquid phase. As is known to the art, the pressure will be a function of the number of carbon atoms of the feed olefin and the temperature. Suitable pressures include from about 10 to 1000 psig.

Olefins which are converted according to the process of the present invention include: cyclopentene, methylcyclopentene, ethylcyclopentene, dimethylcyclopentenes, cyclohexene, methylcyclohexene, ethylcyclohexene, cycloheptene, cyclooctene, and alkyl substituted derivatives of these olefins and mixtures thereof.

The dimerization process described herein may be carried out as a batch type, semicontinuous or continuous operation utilizing a fixed or moving bed catalyst system.

DESCRIPTION OF SPECIFIC EMBODIMENTS

ZSM-12 is described in U.S. Pat. No. 3,832,449, the contents of which is incorporated by reference. Particularly, ZSM-12 has a composition, expressed as mole ratios of oxides, as follows:

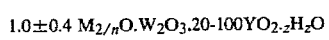

wherein M is a cation, n is the valence of said cation, W is selected from the group consisting of aluminum and gallium, Y is selected from the group consisting of silicon and germanium and z is from 0 to 60. In a preferred synthesized form, M is selected from the group consisting of a mixture of alkali metal cations, especially sodium, and tetraalkylammonium cations, the alkyl groups preferably containing two to five carbon atoms. Alternately, the reaction mixture obtained from the mixing of an alkylamine and a n-alkylhalide or sulfate or other alkylating agent can be used in place of the tetraethylammonium cations. The term reaction mixture encompasses either the mixture of tertiary amine and alkylating agent or a mixture of the aforesaid tertiary amine and alkylating agent.

In a preferred embodiment of ZSM-12, W is aluminum, Y is silicon and the silica/alumina mole ratio is at least 20 and ranges up to about 100.

ZSM-12 zeolites possess a definite distinguishing crystalline structure whose X-ray diffraction pattern shows the following significant lines:

TABLE 1

| Interplanar spacing D(A) | Relative Intensity |
|---|---|
| 11.9 ± 0.2 | M |
| 10.1 ± 0.2 | M |
| 4.76 ± 0.1 | W |
| 4.29 ± 0.08 | VS |
| 3.98 ± 0.08 | M |
| 3.87 ± 0.07 | VS |
| 3.49 ± 0.07 | W |
| 3.38 ± 0.07 | M |
| 3.20 ± 0.06 | W |
| 3.05 ± 0.05 | W |
| 2.54 ± 0.03 | W |

These values were determined by standard techniques.

Zeolites ZSM-12 can be suitably prepared by preparing a solution containing tetraethyl ammonium cations, sodium oxide, an oxide of aluminum or gallium, an oxide of silica or germanium, and water and having a composition, in terms of mole ratios of oxides, falling within the following ranges:

TABLE 2

| | Broad | Preferred | Particularly Preferred |
|---|---|---|---|
| $OH-/YO_2$ | 0.10–0.40 | 0.15–0.25 | 0.17–0.20 |
| $R_4N+/(R_4N+ + Na+)$ | 0.2–0.95 | 0.28–0.90 | 0.3–0.5 |
| $H_2 7/8/OH-$ | 20–300 | 5.0–100 | 80–100 |
| $YO_2/W_2O_3$ | 40–200 | 85–125 | 90–100 | wherein R is ethyl, W is aluminum or gallium and Y is silicon or germanium, and maintaining the mixture until crystals of the zeolite are formed. Thereafter, the crystals are separated from the liquid and recovered. Typical reaction conditions consist of heating the foregoing reaction mixture to a temperature of from about 80° C. to 180° C. for a period of time of from about 6 hours to 150 days. A more preferred temperature range is from about 150° C. to 170° C. with the amount of time at a temperature in such range being from about 5 days to 12 days.

ZSM-12 is preferentially synthesized from a mixture containing a high silica to alumina ratio, for example more than 85 to 1, especially at crystallization temperatures of 212° F. At this temperature, if the silica to alumina ratio drops to 50, conditions favor the formation of beta zeolite.

When the reaction product of triethylamine and diethylsulfate is used in the synthesis of ZSM-12 temperatures of under 175° C. should be maintained. Higher temperatures favor the formation of other zeolites.

The digestion of the gel particles is carried out until crystals form. The solid product is separated from the reaction medium, as by cooling the whole to room temperature, filtering and water washing.

The foregoing product is dried, e.g., at 230° F. for from about 16 to 24 hours. Of course, milder conditions may be employed if desired, e.g., room temperature under vacuum.

ZSM-12 is preferably formed as an aluminosilicate. The composition can be prepared utilizing materials which supply the appropriate oxide. Such compositions include for an aluminosilicate, sodium aluminate, alumina, sodium silicate, silica hydrosol, silica gel, silicic acid, sodium hydroxide and tetraethylammonium compounds, e.g., tetraethylammonium bromide. It will be understood that each oxide component utilized in the reaction mixture for preparing a member of the ZSM-12 family can be supplied by one or more initial reactants and they can be mixed together in any order. For example, sodium oxide can be supplied by an aqueous solution of sodium hydroxide, or by an aqueous solution of sodium silicate, tetraethylammonium cation can be supplied by tetraethylammonium hydroxide, tetraethylammonium bromide or by a mixture of diethylsulfate and triethylamine. The reaction mixture can be prepared either batchwise or continuously. Crystal size and crystallization time of the ZSM-12 composition will vary with the nature or the reaction mixture employed.

ZSM-12 zeolites can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel.

Typical ion exchange techniques would be to contact the ZSM-12 zeolites with a salt of the desired replacing cation or cations. Although a wide variety of salts can be employed, particular preference is given to chlorides, nitrates and sulfates.

Representative ion exchange techniques are disclosed in a wide variety of patents including U.S. Pat. No. 3,140,249; U.S. Pat. No. 3,140,251; and U.S. Pat. No. 3,140,253.

Following contact with the salt solution of the desired replacing cation, the zeolites are then preferably washed with water and dried at a temperature ranging from 150° F. to 1,500° F. for periods of time ranging from 1 to 48 hours or more.

Regardless of the cations replacing the sodium in the synthesized form of the ZSM-12 the spatial arrangement of the aluminum, silicon and oxygen atoms which form the basic crystals lattices of ZSM-12, remains essentially unchanged by the described replacement of sodium or other alkali metal as determined by taking an X-ray powder diffraction pattern of the ion-exchanged material. Such X-ray diffraction pattern of the ion-exchanged ZSM-12 reveals a pattern substantially the same as that set forth in Table 1 above.

The aluminosilicates prepared by the instant invention are formed in a wide variety of particular sizes. Generally speaking, the particles can be on the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the aluminosilicate can be extruded before drying or dried or partially dried and then extruded.

In the case of many catalysts, it is desired to incorporate the ZSM-12 with another material resistant to the temperatures and other conditions employed in organic conversion processes. Such materials include active and inactive materials and synthetic or naturally occurring zeolites as well as inorganic materials such as clays, silica and/or metal oxides. The latter may be either naturally occurring or in the form of gelatinous precipicates or gel including mixtures of silica and metal oxides. Use of a material in conjunction with the ZSM-12, i.e., combined therewith which is active, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. Normally, zeolite materials have been incorporated into naturally occurring clays, e.g., bentonite and kaolin, to improve the crush strength of the catalyst under commercial operating conditions. These materials, i.e., clays, oxides, etc., function as binders for the catalyst. It is desirable to provide a catalyst having good crush strength because in a petroleum refinery the catalyst is often subjected to rough handling, which tends to break the catalyst down into powder-like materials which cause problems in processing. These clay binders have been employed for the purpose of improving the crush strength of the catalyst.

Naturally occurring clays which can be composited with the ZSM-12 catalyst include montmorillonite and kaolin family, which families incude the subbentonites, and the kaolins commonly known as Dixie McNamee-Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the ZSM-12 catalyst can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumiina-magnesia and silica-magnesia-zirconia. The matrix can be in the form of a cogel. The relative proportions of finely divided crystalline aluminosilicate ZSM-12 and organic oxide gel matrix very widely with the crystalline aluminosilicate content ranging from about 1 to 90 percent by weight and more usually, particularly when the composite is prepared in the form of beads in the range of about 2 to about 50 percent by weigh of the composite.

EXAMPLES

The following examples will illustrate the invention. It is to be understood that they are merely illustrative are not to be construed as limiting the scope of the invention.

EXAMPLE 1

The ZSM-12 of this example was prepared by mixing 65 parts "Hi-Sil", 6.3 parts sodium hydroxide, 1 part $Al(NO_3)_3.9H_2O$, 40 parts tetraethylammonium bromide and 310 parts water. The reaction mixture was charged to an agitated autoclave and heated to about 320° F. under autogeneous pressure and held for about 17 hours. The mixture was then cooled to room temperature and 1.1 parts of $NaAlO_2$ and 2.7 parts water were added. The mixture was reheated to about 320° F. and held for an additional 21 hours until crystallization was complete. The crystallized product was filtered and washed. X-ray diffraction analysis reported the product to be 90% ZSM-12. Chemical analysis of the crystalline product was reported as:

| | |
|---|---|
| $SiO_2$ | 95.1% wt |
| $Al_2O_3$ | 1.79% wt |
| Na | 0.34 |
| N | 0.98 |
| C | 7.6 |

This ZSM-12 was then mixed with Kaiser Alumina, in a rate of 65 wt % zeloite and 35 wt % alumina, extruded through a 1/16" die and dried at 250° F.

The extrudate was then calcined in flowing $N_2$ for 3 hours at 1000° F. and then ion-exchanged with 1 N $NH_4NO_3$, washed and dried. This product was calcined for 3 hours at 1000° F. to yield a bond HZSM-12 catalyst.

EXAMPLE 2

The HZSM-12 catalyst of Example 1 (2.0 grams) was charged to a tubular flow reactor and heated to 200° C. under nitrogen.

Cyclohexene was pumped over the catalyst at 24 WHSV (based on catalyst) and 350 psig. Products were collected in a water cooled condenser and analyzed by gas chromatography. The results are presented in Table 3.

TABLE 3

| Dimerization of Cyclohexene over HZSM-12 | | | |
|---|---|---|---|
| Conditions | | | |
| Temperature, °C. | 200 | 250 | 200 |
| Pressure, psig | 350 | 350 | 350 |
| WHSV | 24 | 24 | 24 |
| Time on Stream, hr. | 1 | 2 | 5 |
| Cyclohexene Conversion, Wt. % | 80.3 | 86.3 | 77.4 |
| Product Analysis, Wt. % | | | |
| Cyclohexene dimer | 78.2 | 59.6 | 80.8 |
| Cyclohexene trimer | 14.4 | 25.4 | 13.3 |
| Cyclohexene tetramer | 5.4 | 10.9 | 4.3 |
| Cyclohexene pentamer | 1.6 | 3.5 | 1.3 |
| Cyclohexene hexamer | 0.4 | 0.6 | 0.3 |
| | 100% | 100% | 100% |

EXAMPLE 3

The procedure of Example 2 was followed except that cyclopentene was charged at 400 psig. The results are presented in Table 4.

TABLE 4

| Dimerization of Cyclopentene over HZSM-12 | | |
|---|---|---|
| Conditions | | |
| Temperature, °C. | 200 | 200 |
| Pressure, psig | 400 | 400 |
| WHSV | 7.7 | 23.2 |
| Time on Stream, hr. | 1 | 2 |
| Cyclopentene Conversion, Wt. % | 81.6 | 66.1 |
| Product Analysis, Wt. % | | |
| Cyclopentene dimer | 74.6 | 62.0 |
| Cyclopentene trimer | 14.3 | 28.4 |
| Cyclopentene tetramer | 6.4 | 8.2 |
| Cyclopentene pentamer and higher | 4.7 | 1.4 |

EXAMPLE 4

The procedure of Example 2 was followed except that cyclooctene was charged at 400 psig. The results are presented in Table 5.

TABLE 5
Dimerization of Cyclooctene over HZSM-12

| Conditions | | | |
|---|---|---|---|
| Temperature, °C. | 200 | 200 | 250 |
| Pressure, psig | 400 | 400 | 400 |
| WHSV | 25 | 9 | 9 |
| Time on Stream, hr. | 1 | 2 | 3 |
| Conversion, Wt. % | 28.2 | 36.5 | 54.4 |
| Product Analysis, Wt. % | | | |
| Cyclooctene dimer | 82.9 | 77.8 | 66.9 |
| Cyclooctene trimer | 17.1 | 22.2 | 26.5 |
| Cyclooctene tetramer | 0 | 0 | 6.6 |

EXAMPLE 5

The HZSM-12 of this example was prepared by dissolving 1 part $Al(NO_3)_3.9H_2O$, 3.8 parts NaOH and 20 parts $(C_2H_5)_4NBr$ in 280 parts $H_2O$, adding 35 parts of 40% $(C_2H_5)_4NOH$ and, finally, 65 parts of Hi-Sil (a precipitated silica containing about 90% $SiO_2$). The mixture was charged to a pressure vessel, thoroughly agitated and held at 50° C. for 24 hours, then heated to 160° C. and held at this temperature for 58 hours.

The product was washed and dried at 120° C. It was identified as 95% ZSM-12 by x-ray diffraction with thefollowing chemical analysis:

| | | |
|---|---|---|
| $SiO_2$ | 85.3 wt % | |
| $Al_2O_3$ | 0.80 | |
| $Na_2O$ | 0.40 | |
| N | 0.92 | $SiO_2/Al_2O_3 = 181$ |
| C | n.a. | |
| Ash | 89.2 | |

The material was calcined in flowing $N_2$ for 2 hours at 550° C., followed by 2 hours in air, then ion-exchanged three times with 0.5 N $NH_4Cl$ solution (17 parts solution/1 part of zeolite) for 1 hour each at 80° C., washed and dried at 120° C.

The $NH_4ZSM$-12 product was finally calcined for 3 hours at 550° C. in flowing air to yield HZSM-12.

EXAMPLE 6

In this example, the dimerization selectivity of the HZSM-12 of Example 5 is compared with that of six other catalysts. In each case, 100 cc of cyclohexene and 2.0 g of catalyst were charged to an autoclave reactor. The temperature was increased stepwise in 25°-50° C. increments starting from 100° C. as a rate sufficient to maintain a convenient reaction rate. The pressure was the autogenous system pressure. Samples were periodically removed by means of a dip tube and analyzed by gas chromatography. The results are presented in Table 6.

TABLE 6
Dimerization of Cyclonexene

| | Dimer Selectivity, Wt. %, at 50% Conversion | Dimer Selectivity, Wt. % at 90% Conversion | Polymer Formation Wt. % (% Conversion) |
|---|---|---|---|
| HZSM-12 of Example 5 | 96 | 84 | 5(85) |
| HZSM-5 | 83 | 48 | 17(87) |
| HZSM-38 | 83 | 47 | 17(84) |
| HZSM-20 | 79 | 40 | — |
| REY | 73 | 37 | 11(58) |
| $SiO_2 . Al_2O_3$ | 71 | 28 | 21(88) |
| $H_3PO_4$ | — | — | 22(93) |

The results show the remarkable efficacy of HZSM-12 for the dimerization of cyclohexene.

It will be understood that the foregoing description is merely illustrative of preferred embodiments of the invention of which many variations may be mady by those skilled in the art within the scope of the following claims without departing from the spirit thereof.

I claim:

1. A process for the selective dimerization of cyclo-olefins having from 5 to about 12 carbon atoms which comprises contacting said olefins in the liquid phase with ZSM-12 at temperatures from about 75° C. to about 400° C.

2. The process of claim 1 wherein said contacting is carried out at a WHSV, based on zeolite, of from about 1 to about 100.

3. The process of claim 1 wherein a portion of the original cations associated with the zeolite are replaced by another cation.

4. The process of claim 3 wherein the replacing cation is a metal cation.

5. The process of claim 4 wherein the metal cation is nickel.

6. The process of claim 1 wherein ZSM-12 used is in the H-form.

7. The process of claim 1 wherein the zeolite is incorporated in a matrix.

8. The process of claim 1 wherein the pressure is sufficient to maintain the system in the liquid phase.

9. The process of claim 1 wherein the olefin feed is selected from the group consisting of cyclopentene, methylcyclopentene, cyclohexene, methylcyclohexene, cycloheptene, cyclooctene.

10. The process of claim 1 wherein said dimerization is carried out in an autoclave reactor.

11. The process of claim 1 wherein the temperature is from about 100° to about 300° C.

* * * * *